(12) United States Patent
Wang et al.

(10) Patent No.: US 9,795,464 B2
(45) Date of Patent: Oct. 24, 2017

(54) ADAPTER AND TIP FOR AN AIR AND WATER DENTAL SYRINGE DEVICE

(71) Applicant: Pac-Dent International, Inc., Walnut, CA (US)

(72) Inventors: Daniel Wang, Royland Heights, CA (US); Taosheng Hu, Jiangsu (CN); Bo Tao, Chino, CA (US); Xiao Yang, Arcadia, CA (US)

(73) Assignee: PAC-DENT INTERNATIONAL INC., Brea, CA (US)

( * ) Notice: Subject to any disclaimer, the term of this patent is extended or adjusted under 35 U.S.C. 154(b) by 55 days.

(21) Appl. No.: 14/694,840

(22) Filed: Apr. 23, 2015

(65) Prior Publication Data

US 2016/0310247 A1 Oct. 27, 2016

(51) Int. Cl.
*A61C 17/00* (2006.01)
*A61C 17/02* (2006.01)

(52) U.S. Cl.
CPC ...... *A61C 17/0202* (2013.01); *A61C 17/0217* (2013.01)

(58) Field of Classification Search
USPC .......................................................... 433/80
See application file for complete search history.

(56) References Cited

U.S. PATENT DOCUMENTS

| 5,236,356 | A | 8/1993 | Davis et al. | |
|---|---|---|---|---|
| 6,019,004 | A * | 2/2000 | Conley | B01L 3/0224 422/923 |
| 2009/0171147 | A1 * | 7/2009 | Lee | A61B 17/29 600/104 |
| 2013/0260333 | A1 | 10/2013 | Berkely | |
| 2013/0316299 | A1 * | 11/2013 | Berkely | A61C 17/0202 433/80 |
| 2015/0348320 | A1 * | 12/2015 | Pesach | A61C 9/0033 382/128 |

OTHER PUBLICATIONS

Forest Dental, 1109-010 Syringe quick release with tip, Dec. 9, 2014, http://pdf.medicalexpo.com/pdf/forest-dental/1109-010-syringe-quick-release-w-tip/72232-132974.html.

* cited by examiner

*Primary Examiner* — Nicole F Johnson

(57) ABSTRACT

A dental syringe device that provides air and water to a dental patient. The device includes an adapter that connects a dental tip to a dental syringe body. The dental syringe body provides a conventional syringe body with a handle for a dentist to hold onto and a source of air and water. The tip delivers the air and water to the dental patient. The adapter is an improved adapter having a unique release and attachment component allowing for a quick connect and disconnect between the dental syringe body and the tip. The tip advantageously includes an inner portion with large and uniform air channels for smooth transfer of air and an outer portion made from a rigid plastic that provides an improved cheek retraction feature.

15 Claims, 2 Drawing Sheets

ADAPTER AND TIP FOR AN AIR AND WATER DENTAL SYRINGE DEVICE

BACKGROUND OF THE INVENTION

1. Field of Invention

The present invention relates generally to delivering air and water from a dental syringe device to a dental patient, and specifically, to an improved tip of the device and adapter of the device that connects a dental syringe body of the device to the tip.

2. Description of Related Art

Syringes mechanically pump liquid or gas through a cylindrical tube, referred to as a barrel, using a mechanical plunger that can be pushed and pulled. Syringes include a tip, also referred to as a needle or nozzle, that dispense the liquid or gas pumped through the tube. Syringes are often used to administer medical injections, apply compounds such as glue, and extract liquid samples from a medial patient such as withdrawing blood from a vein.

In the dental field, a dental engine is located nearby the patient and the dentist, where the dental engine is a large appliance that typically includes a small table to hold an instrument tray, a light, a computer display, a small faucet, and mouth rinsing sink. Additionally, the dental engine that delivers power to the dentist's hand tools such as an ultrasonic cleaning apparatus and an air and water dental syringe device.

The air and water dental syringe device supplies water, air, or mist to the patient's mouth to clean away debris from the area that the dentist is working on. The term dental syringe could also refer to local anesthetic syringe that delivers drugs to a dental patient.

Conventional air and water dental syringe devices are handheld and deliver air and water under pressure. These devices contain valves and buttons on the body of the device that allow for selective discharge of water or air. These devices are widely used by dentists, orthodontists, oral surgeons, dental assistants, and dental hygienists and similar personnel.

It is very important to keep the dental syringe devices clean. Of principal concern, is avoiding cross contamination, which is the undesirable transfer of bacteria or virus from one patient to another through the reuse of the device. Traditionally, syringe tips were all metal, reusable, and required cleaning before reuse. More recently, to avoid cross contamination, most dental syringe tips are disposable and plastic. The disposable tips eliminate the risk of cross contamination between patients if a dental tip is not sufficiently cleaned before reuse unlike the conventional all metal tip. Using a new disposable tip for every single use is currently the most desirable approach to reduce cross contamination.

A problem with disposable dental syringe devices is effectively connecting and disconnecting the tip to the dental syringe body. The dental syringe body is often times referred to in the art simply as a dental syringe. It is desirable for the tip and body to adapt to each other easily and quickly. Most early dental syringe devices did not have an adapter, which presented a risk of cross contamination from reuse of the dental syringe body. More recently, many of the dental syringes include an adapter which is easier to clean and replace. However, conventional adapters are not easy to use because they do not allow the tips to be quickly and easily connected and disconnected from the body of the dental syringe.

Another problem with conventional dental syringe devices is achieving sufficient and consistent air flow through the device. Conventional tips have air channels with very small and uneven diameters which produce inadequate air-flow which generate uneven water sprays.

A further problem with conventional dental syringe devices is that new disposable tips are made of a plastic that does not provide the cheek retraction function provided by the traditional all metal tips. The cheek retraction function is where a device opens a patient's cheeks away such that the medical professional can see and access an area of interest within the patient's mouth during a procedure. The disposable plastic tips which are currently in use compromise the cheek retraction function because the bends too easily and thus does not keep the patient's mouth open. Metal tips are currently not a feasible solution due to cost and environmental waste concerns.

U.S. Patent Publication number 2013/0260333, abandoned, by Berkely is directed to a seamless air/water dental syringe tip adapter systems and conversion methods. Specifically, conversion assemblies enable an air/water dental syringe adapted for connection to an existing tip such as an autoclavable tip to instead receive disposable tip. A conversion kit includes a cap subassembly with a cap body having a distal opening into which the disposable tip is inserted, and an adapter subassembly having a proximal end configured for connection to the syringe body and a distal end configured for coupling to the cap subassembly. The adapter subassembly includes one or more components with cut-outs, grooves or channels to direct air and water from the syringe body to the air-carrying channels and water-carrying tube of the disposable tip through the cap subassembly. However, Berkely discloses a conversion assembly and not a component for connecting and disconnecting the tip.

Non-patent literature by Forest Dental, entitled syringe quick release with a tip, includes a dental syringe having a tip, a syringe body, and an adapter assembly. The literature describes a quick release button for the removing of the tip, although the tip appears to be removed by rotating a slot on an adapter until it is aligned with a pin on the adapter to release the tip.

U.S. Pat. No. 5,236,356 issued to Davis is directed to a dental syringe tip and adaptor. The device includes a clear rigid plastic syringe tip having a central water passageway and three arcuate section air passageways disposed circumferentially about the water passageway. A rigid plastic is preferred to fulfill the need to use the tip for continued retraction of the cheek, and tongue by the dental operator. A novel adaptor is used to mount the syringe tip to the handpiece body. The air and water orifices in the tip are quite small, so any plugged of the tip orifices results in both a loss of spray pressure as well as a loss of spray accuracy. A more sterile dental environment is created as well as the flow of air, water or spray form the syringe to the oral cavity. However, Davis falls short of truly simplifying the connecting and disconnecting of the tip to the syringe body and a tip could be bent and allows proper air flow.

SUMMARY OF THE INVENTION

A dental syringe device that provides air and water to a dental patient. The device includes an adapter that connects a dental tip to a dental syringe body. The dental syringe body provides a conventional syringe body with a handle for a dentist to hold onto and a source of air and water. The tip delivers the air and water to the dental patient. The adapter is an improved adapter having a unique release and attachment component allowing for a quick connect and disconnect between the dental syringe body and the tip. The tip advantageously includes an inner portion with large and uniform air channels for smooth transfer of air and an outer portion made from a rigid plastic that provides an improved cheek retraction feature.

The adapter, which can be referred to as a dental air and water syringe tip adapter assembly, enables the air and water syringe body to receive the tip having a central water channel surrounded by air channels. The adapter includes a housing having a distal end for removably receiving the rearward portion of the disposable tip and a proximal end to be screwed onto the syringe body. The adapter also includes a mechanical latch mechanism for a quick connection and disconnection between the adapter and the syringe tip. The adapter further includes an insert having a distal end insertable into the housing for receiving the rearward portion of the syringe tip and a proximal end insertable into the syringe body, with one or more seal elements on the outer wall of insert. The device also includes one or more components with cut-outs, grooves, and channels to direct air and water from the syringe body to the water and the air channels of the syringe tip through the adapter. The housing and the insert define an axially extending bore to receive the rearward portion of the tip for coupling the water port of the syringe to the water channel of the tip. The air channel cut-outs on the insert coupling the air port of the syringe to the air channel of the tip.

An advantage of the dental syringe device is a release component that allows the tip and the adapter connected to the syringe body to quickly and easily adapt to each other. The release component can be a manually depressible button that quickly disconnects the tip when pressed and quickly connects the tip when pressed and released. To further improve adaptation, the syringe tip has a locking groove that couples with the adapter to prevent the syringe tip from dislodging. Further, the syringe tip has an additional groove, referred to herein as a secure seating indicator, to provide visual affirmation to the medical professional that the syringe tip is properly seated in the adapter.

Another advantage is large and uniform air channels that increase the air flow through the adaptor and the tip to achieve sufficient and consistent air flow and even water sprays. Further, the larger inner diameter of the syringe tip further increases its rigidity, enabling the user to use it as a cheek retraction device during use. Moreover, this invention has a bigger cross-section as well as more air channels, which allows for larger air output. In one embodiment, the tip's outer diameter is no less than 4 millimeters (mm), where this thick outer diameter increases the rigidity of the syringe tip and enables the user to use it as a cheek retraction device, although it is still desirable to allow for a large volume of output of air and water to pass there through, as well.

A further advantage of the dental syringe is a plastic exterior of the tip that is semi-rigid, which is rigid enough to provide a cheek retraction function that is not provided by disposable tips which bend easily and do not keep the patient's mouth open, but can be bent under sufficient pressure. In one embodiment, the syringe tip's outer tubing is made of hard plastics, and the inner tubing is made of stainless steel, and this combination further improves the cheek retraction function of the tip by increasing its overall rigidity and enabling the user to use the tip as a cheek retraction device. With this, the dentist can see and access an area of interest within the mouth during a procedure.

The foregoing, and other features and advantages of the invention, will be apparent from the following, more particular description of the preferred embodiments of the invention, the accompanying drawings, and the claims.

DETAILED DESCRIPTION OF THE INVENTION

Figure 1:
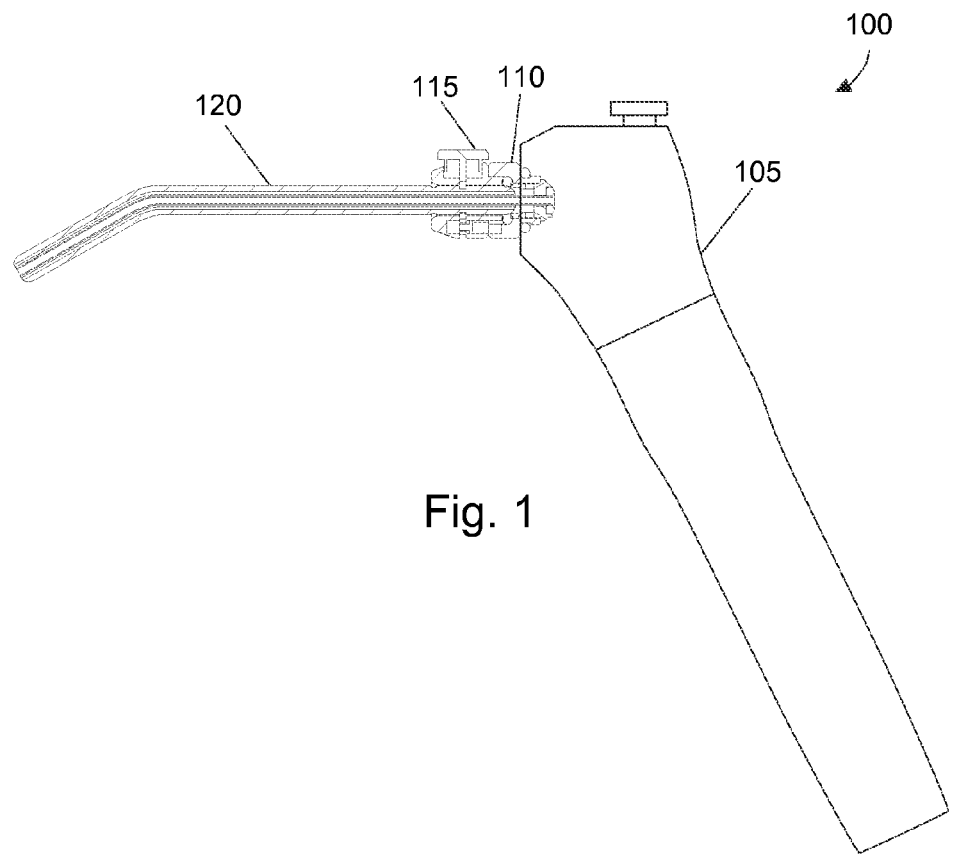
FIG. 1 illustrates a cut-away side view of a dental syringe device according to one embodiment of the invention.

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

Further features and advantages of the invention, as well as the structure and operation of various embodiments of the invention, are described in detail below with reference to the accompanying FIGS. 1-4, wherein like reference numerals refer to like elements. Although the illustrations illustrate an air and water syringe, one with skill in the art could add an additional channel for mist, referred to as a three way dental syringe, without departing from the spirit of the invention.

Embodiments of the invention provide a dental syringe device with an adapter assembly that may be quickly connected or disconnected to and from a tip, such that the tip is connected to or disconnected from the dental syringe body. The adapter has a proximal end, near the dentist, that is connected to the dental syringe and a distal end, near the patient, that allows the syringe tip to be easily connected or disconnected. Also, the adapter has a through channel that allows water to pass from the dental syringe body to the dental syringe tip. The adapter also has several cut-out air channels for air to pass from the dental syringe body to the dental syringe tip. A plurality of seal elements inside the adapter provide a fluid-and-air tight seal. The tip also provides separate sealed air and water channels.

Because the adapter can be replaced without changing the dental syringe body, the adapter significantly reduces the costs of dental procedures and prevents contamination of the dental syringe body. Furthermore, the adapter has a working mechanism that allows the syringe tip to be quickly and effortlessly connected to and disconnected from the syringe. Further, the syringe tip has a secured seating indicator which is convenient for operation.

FIG. 1 illustrates a cut-away side view of a dental syringe device 100 according to one embodiment of the invention. The device 100 (e.g., air and water dental syringe device, dental instrument, etc.) includes a dental syringe body 105, an adapter 110 having a release and attachment component 115, and a tip 120. The device 100 allows a dentist to deliver air and water to a patient. Further, the device 100 provides an improved adapter 110 for quicker changing of disposable syringe tips and an improved tip 120 with improved cheek retraction and air flow.

The dental syringe body 105 (e.g., dental syringe, handle, etc.) is a conventional dentist tool know by those with skill in the art and thus is not shown in a cutout view. The body 105 includes handle for a dentist to hold, an electronic source of source of air and water, and valves or buttons for the dentist to press for delivering the air and water. Although the body 105 is often times referred to by those in the art as simply a dental syringe, for clarity, the dental syringe body 105 is referred to herein with the term body and the entire dental syringe device 100 is referred to herein with the term device.

The adapter 110 (e.g., adapter assembly, etc.), shown in a cut-away view, connects the dental syringe body 105 to the syringe tip 120. The adapter 110 is an improvement over conventional adapters in that it provides a release and attachment component 115.

The release and attachment component 115 (e.g., component, release component, release button, etc.) provides a faster connection and disconnection of the tip 120 from the body 105. The release and attachment component 115 can be a manually depressible button that quickly releases the tip when pressed and also allows for a quick attachment when pressed and released. Although the details of release and attachment component 115 can be seen in the cutout side view of FIG. 1, the specific components are shown and described in more detail in the exploded view of FIG. 2.

The tip 120 (e.g. dental tip, nozzle, dental syringe tip, etc.), also shown in cut-away view, connects to the body 105 through the adapter 110. The tip 120 delivers air and water to the dental patient. As described further with respect to FIG. 4, the tip 120 includes larger and more uniform air channels to increase the air flow and a semi-rigid plastic on the exterior of the tip that while possible to be bent, still provides the cheek retraction function not provided by disposable tips. The tip 120 may be either co-extruded or assembled.

Figure 2:
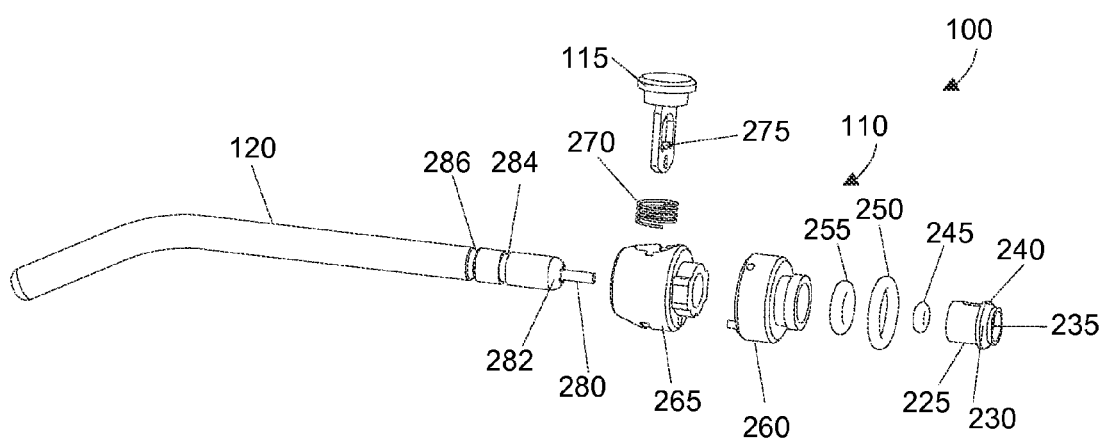
FIG. 2 illustrates an exploded view of an adapter and tip of the device according to one embodiment of the invention.

FIG. 2 illustrates an exploded view of adapter 110 and the tip 120 of the device 100 according to one embodiment of the invention. The adapter 110 includes an insert 225 having a ferrule 230, a central opening 235, and side cutouts 240. The adapter 110 further includes a plurality of seals 245, 250, 255, a proximal housing 260, a distal housing 265, a spring 270, a locking slide 275, and the release and attachment component 115. The tip 120 includes an extended water tube 280, a base surface 282, a locking groove 284, and a secure seating indicator groove 286. The adapter 110 and tip 120 allow for quicker changing of disposable syringe tips and better cheek retraction and air flow.

The insert 225 has a distal end, the side closer to the patient, insertable into the proximal part of the housing 260, and a proximal end, the side closer to the dentist, insertable into the syringe body 105. The insert 225 is configured to receive the extended water tube 280 of the syringe tip 120. The insert 225 further includes a cup-shaped ferrule 230 which is a metal ring or cap that receives the rearward portion of the tip 120, with a central opening 235 through which water passes to the water channel 280 of the syringe tip 120, and one or more side cutouts 240 through which air passes into air channels of the syringe tip 120. The water and air channels are illustrated and described in more detail in FIG. 4.

The plurality of seals 245-255 advantageously provide an improved separation between the air and the water in the adapter 110. The seal element 245 is circumferentially disposed on the proximal end of the insert 225, engaging the outer wall of the water tube 280 and rearward portion of the syringe tip 120 upon insertion of the syringe tip 120 into the adapter 110 to form a fluid-and-air tight seal between the syringe tip 120 and the syringe body 105.

The seal element 250 is circumferentially disposed about an outer wall of the proximal part of the housing 260, the seal element 250 engaging an inner wall of a syringe body 105 when the housing is screwed onto the syringe body 105 to form a fluid-and-air tight seal between the housing 260 and the syringe body 105.

The seal element 265 is circumferentially disposed about an inner wall of the proximal part of the housing 260, as well as engaging an outer wall of the insert 225 upon insertion of the insert 225 into the proximal part of the housing 260 to form a fluid-and-air tight seal between the insert 225 and the housing 260.

The proximal and distal housing 260, 265 connect to form a single housing. The proximal housing 260 includes the plurality of seals 245-255 and the insert 225. The distal housing 265 includes the release and attachment component 115, the spring 270, and locking slide 275. The proximal housing 260 is to be screwed on to the syringe body 105. The distal part of the housing 265 is to removably attachable to the rearward portion of the disposable syringe tip 120.

The release and attachment component 115 (e.g., release component, manually depressible release button, button, etc.) couples with the wholly enclosed locking slide 275 (e.g., movable locking slide, mechanical latch mechanism, etc.), with the spring 270 (e.g., spring socket) on the release and attachment component 115, which work together to connect or disconnect the syringe tip 120. When the button 115 is depressed, the spring 270 adapts and the locking slide 275 is retracted, so that the syringe tip 120 can be connected or disconnected to the adapter assembly 110. When the button 115 is released, the spring 270 adapts to urge the locking slides 275 back to the locking position and couples with the locking groove 284 on the syringe tip 120, to prevent the syringe tip 120 from moving.

The manually depressible release button 115, together with the wholly enclosed movable locking slide 275 and the spring socket 270, allow the disposable tip 120 to be connected or disconnected to the adapter 110. When the button 115 is depressed, it urges the slide 275 to be retracted into the channel and when the button is released it prevents the disposable tip 120 from moving as the spring 270 adapted to urge the locking slide 275 back to the locking position and to be coupled with the groove 284 on the disposable tip 120. The internal locking groove 284 is seated inside the bore of the distal housing 265.

The base surface 282 on the proximal end of the syringe tip 120 has openings for the air source of the syringe body 105. The water tube 280 extends outwardly from the base surface 282 to the water port of the syringe body 105. In one embodiment, the syringe tip 120 is made of hard plastics and the water tube 280 is made of stainless steel.

The plurality of grooves 284, 286 include the locking groove 284 and the secure seating indicator groove 286. The grooves 284, 286 include two or more circumferential grooves around the periphery of the tip 120 and spaced axially forward on the tip's proximal end. The locking groove 284 is configured to pass through and engage with the locking slide 275. The locking groove 284 further improves adaptation between the tip 120 and the dental syringe body 105 as the locking groove 284 couples with the locking slide 275 being pressed down by the spring 270 which prevent the syringe tip 120 from dislodging. The locking groove 284 couples with the locking slide 275 when the button 115 is released and the spring adapts to urge the locking slide 275 back to the locking position to prevent the syringe tip 120 from moving.

The secure seating indicator groove 286 (e.g., secure seating indicator) provides visual affirmation to the medical professional of proper seating of the syringe tip. The secure seating indicator groove 286 provides confirmation of proper seating of the syringe tip 120. In one embodiment, the secure seating indicator 286 is a line, as opposed to a groove.

Figure 3:
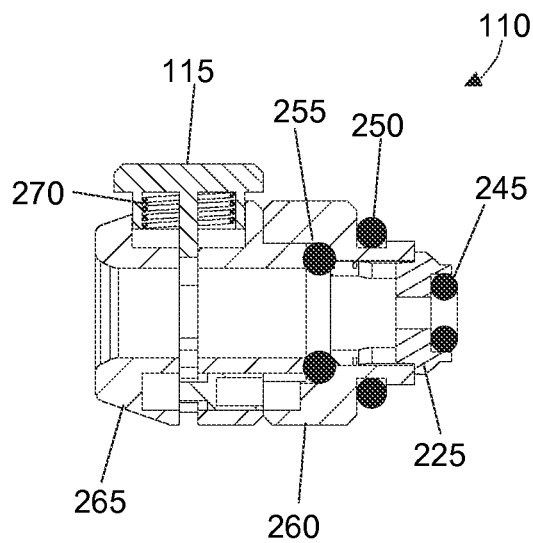
FIG. 3 illustrates a closer cut-away view of the adapter of the device according to one embodiment of the invention.

FIG. 3 illustrates a closer cut-away view of the adapter 110 of the device 100 according to one embodiment of the invention. Like illustrated and described in FIG. 2, the adapter 110 includes the insert 225, the plurality of seals 245, 250, 255, the proximal and distal housings 260, 265, the spring 270, and the release and attachment component 115.

The insert 225, the proximal part of the housing 260, and the distal part of the housing 265 define an axially extending bore to receive the syringe tip 120 for coupling the water port of the syringe body 105 to the water tube 280 of the syringe tip 120. The seal elements 245-255 form a fluid-and-air tight seal between the syringe tip 120, the housing 260, 265, and the syringe body 105. The release and attachment component 115, the locking slide 275 together with the spring 270 form a connecting and disconnecting mechanism to easily and quickly release or connect to the syringe tip 120.

Figure 4:
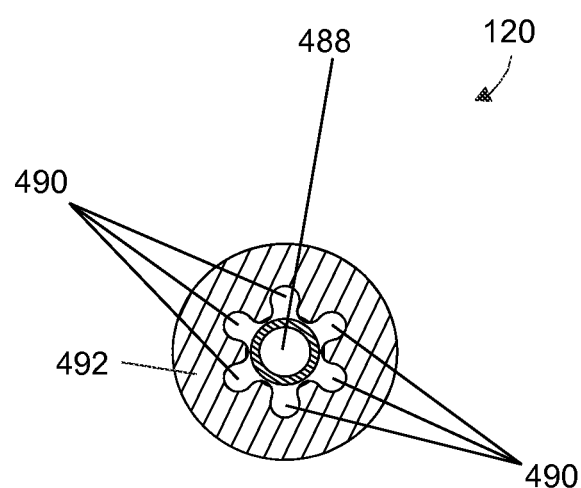
FIG. 4 illustrates a cut-away view of a distal end of the tip of the device according to one embodiment of the invention.

FIG. 4 illustrates a cut-away view of a distal end of the tip 120 of the device 100 according to one embodiment of the invention. The tip 120 includes a water channel 488 within the central water tube 280, a plurality of air channels 490, and a semi-rigid plastic 492. The syringe tip 120 has the water channel 488 surrounded by the plurality of air channels 490.

The water tube 280 connects to a water port of the syringe body 105. The water tube 280 delivers water to the dental patient through the water channel 488 and is conventional component known by those with skill in the art.

The air channels 490 (e.g., cutouts) allow for the transfer of air from the syringe body 105. The air channels 490 are illustrated as six air channels surrounding the water tube 488. In some embodiments, the number of the air channels 490 is preferably 6 or 7. The air channels are larger and more uniform than in conventional dental syringe devices, which increase the air flow through the adaptor and the tip to achieve sufficient and consistent air flow and even water sprays. In one embodiment, the tip's outer diameter is no less than 4 millimeters.

The dental syringe device 100 supplies air and water through the tip 120 having the central water channel 488 surrounded by the plurality of air channels 490. The tip 120 also has the proximal base surface 282 with openings to the air channels 490 and the water tube 280 extending outwardly form the base surface 282. In one embodiment, both channels 488, 490 are autoclavable so that the syringe tip 120 can be autoclaved in between operations. In embodiments, the tip's autoclavability by can be selected from materials including, but not limited to, polycarbonate (PC), stainless steel core, polyether ether ketone (PEEK), copolyster, etc.

The semi-rigid plastic 492 on the exterior of the tip 120 is rigid enough to provide the cheek retraction function not provided by disposable tips which bend too easily and do not keep the patient's mouth open. The term semi-rigid is used because although the tip 120 cannot be easily bent, it does not mean it is so rigid that it is not possible to bend. The semi-rigid plastic is just rigid enough to be used as a cheek retraction device. In one embodiment, the syringe tip's outer tubing is made of hard plastic, and the inner tubing is made of stainless steel, and this combination further improves the cheek retraction function of the tip by increasing its overall rigidity. With this, the dentist can see and access an area of interest within the mouth during a procedure.

In one embodiment, the outer diameter of the syringe tip 120 is no less than 4 mm, which allows for large volume of output of air and water, as well as increasing the rigidity of the syringe tip and enabling the user to use it as a cheek retraction device. The larger inner diameter of the syringe tip 120 further increases its rigidity, enabling the user to use it as a cheek retraction device during use. Moreover, this invention has a bigger cross-section as well as more air channels, which allows for larger air output.

It is to be recognized that depending on the embodiment, certain acts or events of any of the methods described herein can be performed in a different sequence, may be added, merged, or left out altogether (for example, not all described acts or events are necessary for the practice of the method). Moreover, in certain embodiments, acts or events may be performed concurrently, for example, through multi-threaded processing, interrupt processing, or multiple processors, rather than sequentially.

It should be understood that the invention is not limited to the embodiments set forth herein for purposes of exemplification, but is to be defined only by a fair reading of the appended claims, including the full range of equivalency to which each element thereof is entitled. Although the invention has been described with reference to the above examples, it will be understood that modifications and variations are encompassed within the spirit and scope of the invention. Accordingly, the invention is limited only by the following claims.

What is claimed is:

1. An adapter comprising:
   a proximate end configured to attach to a dental syringe body;
   a distal end configured to attach to a tip, wherein the tip is in fluid communication with the dental syringe body through the adapter;
   a release component configured to release the tip from the adapter, wherein the release component comprises a manually depressible release button, wherein the release component is in contact with a spring, wherein the spring creates a spring pressure applied to the release component creating a release component pressure, the release component pressure applying pressure on the tip to lock the tip in place; and
   a movable locking slide on the release component for connection and disconnection between the adapter and the tip, the movable locking slide in contact with the spring and creating the release component pressure, wherein the release component being depressed into the spring releases the tip, and wherein the release component being released locks the tip in place, wherein the movable locking slide connects with a locking groove on the tip to lock the tip in place.

2. The adapter of claim 1, wherein the tip comprises air channels having a uniform diameter.

3. A device comprising:
a dental syringe body;
an adapter configured to attach to the dental syringe body;
a tip configured to attached to the adapter, wherein the tip is in fluid communication with the dental syringe body through the adapter; and
a release component coupled to the adapter, wherein the release component is configured to release the tip from the adapter, wherein the release component comprises a manually depressible release button, wherein the release component is in contact with a spring, wherein the spring creates a spring pressure applied to the release component creating a release component pressure, the release component pressure applying pressure on the tip to lock the tip in place; and;
a movable locking slide on the release component for connection and disconnection between the adapter and the tip, the movable locking slide in contact with the spring and creating the release component pressure, wherein the movable locking slide connects with a locking groove on the tip to lock the tip in place.

4. The device of claim 3, wherein the tip comprises air channels having a uniform diameter.

5. The device of claim 3, wherein the tip comprises semi-rigid plastic on an outer portion of the tip.

6. The device of claim 3, wherein the release component is further configured to attach the tip to the adapter.

7. The device of claim 3, wherein the tip comprises air channels having a diameter that is larger than a radius of a central water channel in the tip.

8. The device of claim 3, wherein the adapter comprises a plurality of seals.

9. The device of claim 3, wherein the tip comprises a secure seating indicator to indicate that the tip is securely attached to the adapter.

10. The device of claim 3, wherein the tip comprises a central water channel surrounded by air channels.

11. The device of claim 3, wherein the adapter comprises a housing having a distal end for receiving a rearward portion of the tip and a proximal end to be screwed onto the dental syringe body.

12. A tip comprising:
a distal end configured to interact with a patient; and
a proximate end configured to attach to an adapter, wherein the tip is in fluid communication with a dental syringe body through the adapter,
wherein the tip comprises semi-rigid plastic on an outer portion of the tip, wherein the tip comprises a locking groove configured to receive a movable locking slide on the adaptor to lock the tip in place.

13. The tip of claim 12, wherein the tip comprises air channels having a uniform diameter.

14. The tip of claim 12, wherein an outer diameter of the tip is no less than 4 millimeters.

15. The tip of claim 12, wherein the tip is autoclavable and the autoclavability is selected from polycarbonate (PC), stainless steel core, polyether ether ketone (PEEK), or copolyster.

* * * * *